United States Patent [19]

Stevens et al.

[11] Patent Number: 5,735,825
[45] Date of Patent: Apr. 7, 1998

[54] SYRINGE PLUNGER TIP

[75] Inventors: Brian W. Stevens, Pleasant Grove; Darryl Kent Backman; Garlyn W. Hendry, both of Salt Lake City, all of Utah

[73] Assignee: Merit Medical Systems, Inc., South Jordan, Utah

[21] Appl. No.: 620,386

[22] Filed: Mar. 22, 1996

[51] Int. Cl.⁶ .................................................. A61M 5/00
[52] U.S. Cl. ...................................... 604/218; 604/222
[58] Field of Search .............................. 604/218, 187, 604/222, 230

[56] References Cited

U.S. PATENT DOCUMENTS

| | | | |
|---|---|---|---|
| 3,809,082 | 5/1974 | Hurschman | 128/218 |
| 4,215,701 | 8/1980 | Raitto | 128/763 |
| 4,266,557 | 5/1981 | Merry | 128/763 |
| 4,354,507 | 10/1982 | Raitto | 128/763 |
| 4,363,329 | 12/1982 | Raitto | 128/765 |
| 4,986,820 | 1/1991 | Fischer | 604/218 |
| 5,314,416 | 5/1994 | Lewis et al. | 604/219 |
| 5,395,345 | 3/1995 | Gross | 604/187 |
| 5,397,313 | 3/1995 | Gross | 604/218 |

*Primary Examiner*—John D. Yasko
*Attorney, Agent, or Firm*—Workman Nydegger Seeley

[57] ABSTRACT

A sealing cap is provided for attachment to the end of a syringe plunger. The sealing cap has an annular sidewall with an annular first sealing wing projecting distally therefrom, an annular second sealing wing positioned proximal of the first sealing wing and projecting proximally, and an annular sealing ridge encircling and radially projecting out from between the first sealing wing and the second sealing wing. The sealing cap further includes an interior cavity having an annular side surface aligned with the annular sidewall. A side groove is recessed within the side surface so as to be aligned slightly proximal of the annular sealing ridge. The distal end of a syringe plunger has a head mounted thereon that is substantially complementary to the configuration of the internal cavity of the sealing cap. More specifically, a tapered ridge is formed on the periphery of the head to complementarily be received within the side groove. As a positive pressure is created against the sealing cap, the first sealing wing flexes against the interior surface of the barrel and the annular sealing ridge urges against the interior surface of the barrel, thereby increasing the effective seal. As a negative pressure is formed within the barrel, the second sealing wing flexes against the interior surface of the barrel to increase the effective seal.

49 Claims, 6 Drawing Sheets

SYRINGE PLUNGER TIP

BACKGROUND OF THE INVENTION

1. The Field of the Invention

The present invention relates to syringes and, more specifically, medical syringes having a syringe plunger with an improved tip for sealing against the interior surface of a syringe barrel.

2. The Relevant Technology

A variety of different syringes are used in the medical field. A typical syringe comprises a tubular barrel having an access opening formed at one end, and a smaller discharge opening formed at the opposing end. The lead end of an elongated plunger is received within the access opening of the barrel so as to be slidable within the barrel. Attached to the lead end of the plunger is a flexible sealing member that snugly seals against the interior surface of the barrel. A needle or threaded member is usually attached to the discharge opening on the barrel. The needle can be used to penetrate a surface while the threaded member can be used to attach the syringe to another medical device, such as a catheter.

During use, the discharge end of the syringe is initially placed in contact with a fluid. For example, the needle on the syringe can be inserted into a liquid medication. As the plunger is retracted within the barrel, a process known as aspiration, a negative pressure is formed within the end of barrel so as to cause the fluid to be drawn into the barrel. The syringe can then be moved to a second location where advancing the plunger within the barrel causes the fluid to be pushed or expressed out the discharge end of the barrel.

Syringes come in a variety of different sizes and configurations each having unique properties for their intended use. For example, at times it is necessary to use a syringe that is capable of withstanding high pressures within the barrel. Such high pressures may be encountered when it is necessary to introduce a large amount of fluid into a body of an individual in a short period of time. High syringe pressures may also be encountered when it is necessary to insert a large amount of fluid into relatively small structure, such as the small, narrow tube of a catheter.

To accommodate the above situations, it is necessary that the seal between the sealing member and the barrel be sufficiently strong to prevent leaking. Failure of the seal would prevent at least a portion of the fluid from being discharge and, as such, could be critical in an emergency situation.

To accommodate the formation of high pressures, conventional syringes use enlarged sealing members which are compressed within the barrel such that a large lateral force is continually urged against the interior surface of the barrel. As such, the syringe is able to withstand high pressures within the barrel without failure of the seal. The problem associated with such syringes, however, is that the increased force pushing on the interior surface of the barrel increases the friction between the sealing member and the barrel. As a result, it is more difficult to advance the plunger within the barrel. Furthermore, increasing the friction between the sealing member and the barrel decreases the medical practitioners ability to feel the pressure on the fluid within the syringe barrel.

Alternative types of syringes are made exclusively to enable a medical practitioner to feel any pressure variance on the fluid in the barrel. For example, administration of an epidural anesthesia requires a needle to be located within an epidural space located around the spinal cord. To help determine the exact location of the epidural space, medical practitioners use syringes which have very low friction between the sealing member and the barrel. As a result, a medical practitioner is able to determine the location of the needle tip by sensing through the plunger the pressure variations within the various body spaces.

One type of syringe that is designed for such use is a glass syringe. Glass syringes, however, are extremely expensive as they are handmade and can shatter if dropped. Other types of syringes which accommodate the ability to feel the fluid pressure within the barrel have been made by using sealing members which only slightly engage the interior surface of the barrel, resulting in a very low friction force. One drawback, however, is that such syringes are unable to withstand the injection of fluids at high pressures without failure of the seal.

Other syringes are designed to carefully dispense micro amounts of medication. Such syringes, however, often encounter the problem of "stiction." Stiction refers to the phenomenon that a syringe will jump or skip during small advancement of the plunger. As a result, more medication is deliver then is desired. Stiction occurs because a larger amount of energy is needed to overcome the static force between the barrel and sealing member than is needed to slide the plunger the desired distance. To design a syringe with low stiction, it is again necessary to minimize the friction force between the sealing member and the barrel. As is evidenced from the foregoing examples, however, syringes found in the prior art that are designed to have low friction typically do so at the expense of reducing the ability of the syringe to seal under high pressure. Conversely, syringes found in the prior art that are designed for high pressure applications typically to do at the expense of reducing the syringes' ability to have a "sensitive feel" and low stiction.

As a result of what appears to be mutually exclusive properties for syringes, a medical facility is required to purchase and store a vast array of different types of syringes having different properties. This large number of syringes increases overhead costs and takes up valuable storage space. Furthermore, the large number of syringes complicates medical producers since the medical practitioners must ensure that they have the proper syringe for the proper procedure.

OBJECTS AND BRIEF SUMMARY OF THE INVENTION

Accordingly, it is an object of the present invention to provide improved syringes.

It is another object of the present invention to provide improved syringes that can withstand high pressures within the barrel without failure of the seal between the barrel and the plunger.

It is yet another object of the present invention to provide improved syringes that have low friction between the plunger and barrel under low pressures.

Another object of the present invention is to provide improved syringes that minimize stiction at low pressures.

It is still another object of the present invention to provide improved syringes that are able to both withstand high pressures without failure and have low friction between the plunger and barrel at low pressures.

Still another object of the present invention is to provide improved syringes in which the effectiveness of the seal between the plunger and the barrel increases as the pressure within the barrel increases.

Another object of the present invention is to provide improved syringes in which a single syringe is able to accomplish the task of two or more conventional syringes.

Furthermore, it is another object of the present invention to provide such syringes at a relatively low cost.

Finally, it is another object of the present invention to provide syringes that produce effective seals between the plunger and barrel during both injection and aspiration.

To achieve the foregoing objectives and in accordance with the invention as embodied and broadly disclosed herein, an improved syringe is provided. The syringe includes a barrel having an interior surface defining a lumen longitudinally extending therethrough. The syringe further includes an elongated plunger having a distal end slidably received within the lumen of the barrel. The plunger comprises a conical head positioned at the distal end of the plunger. The conical head radially slopes outward to an annular outer edge.

Mounted on the head of the plunger is a flexible sealing cap. The flexible sealing cap is preferably made of silicone and can be coated with a lubricant. In the preferred embodiment, the flexible sealing cap comprises an annular sidewall having an exterior surface extending between a proximal end and a distal end. A conical crown is mounted on the annular sidewall so as to cover the distal end of the sealing cap.

An annular first sealing wing encircles and radially projects outward in a distal direction from the exterior surface of the sidewall. The first sealing wing preferably projects out at an angle of about 30 degrees relative to the longitudinal axis of the sealing cap. The first sealing wing contacts the interior surface of the barrel when the distal end of the plunger having the flexible sealing cap received thereon is positioned within the barrel.

The flexible sealing cap further includes an annular second sealing wing encircling and radially projecting outward in a proximal direction from the exterior surface of the sidewall. As with the first sealing wing, the second sealing wing also projects at an angle of approximately 30 degrees relative to the longitudinal axis of the sealing cap. The second sealing wing is positioned proximal of the first sealing wing and contacts the interior surface of the barrel when the sealing cap attached to the head of the plunger is received within the barrel.

Radially projecting out from the exterior surface of the sidewall between the first sealing wing and the second sealing wing is an annular sealing ridge. The peak of the sealing ridge may or may not contact the interior surface of the barrel during ambient conditions.

The flexible sealing cap further includes an interior surface defining a cavity within the sealing cap. The cavity is configured to complementarily receive the head of the plunger. As such, the cavity includes an annular side groove configured to complementarily receive the outer edge of the head of the plunger. The side groove is positioned relative to the annular sealing ridge so that the annular sealing ridge radially urges out to increasingly engage the interior surface of the barrel as the plunger is advanced within the barrel to increase the pressure within the barrel.

Finally, an annular end face is positioned at the proximal end of the sealing cap and defines an opening to the cavity through which the head of the plunger can be received within the cavity of the sealing cap.

One of the unique properties of the present inventive syringe is its ability to vary the amount of friction and the effective sealing force between the sealing cap and the barrel. For example, when the syringe is used under relatively low barrel pressures, the tips of the first and second sealing wings only slightly engage the interior surface of the barrel with a minimal amount of force. As such, only minimal friction force occurs. In contrast, however, as the pressure within the barrel increases, the pressure within the barrel acts on the first sealing wing, urging it to flex radially outwardly, so as to apply a greater amount of force against the interior surface of the barrel. The amount of sealing force applied by the sealing wing against the interior surface of the syringe barrel is proportional to the amount of pressure generated within the syringe barrel. Furthermore, the sealing ridge increasingly engages against the interior surface of the barrel. As a result, the effective sealing force between the sealing cap and the interior surface of the barrel increases as the pressure within the barrel increases.

These and other objects, features, and advantages of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained and understood, a more particular description of the invention briefly described above will be rendered by reference to a specific embodiment thereof which is illustrated in the appended drawings. Understanding that these drawings depict only a typical embodiment of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

Figure 1:
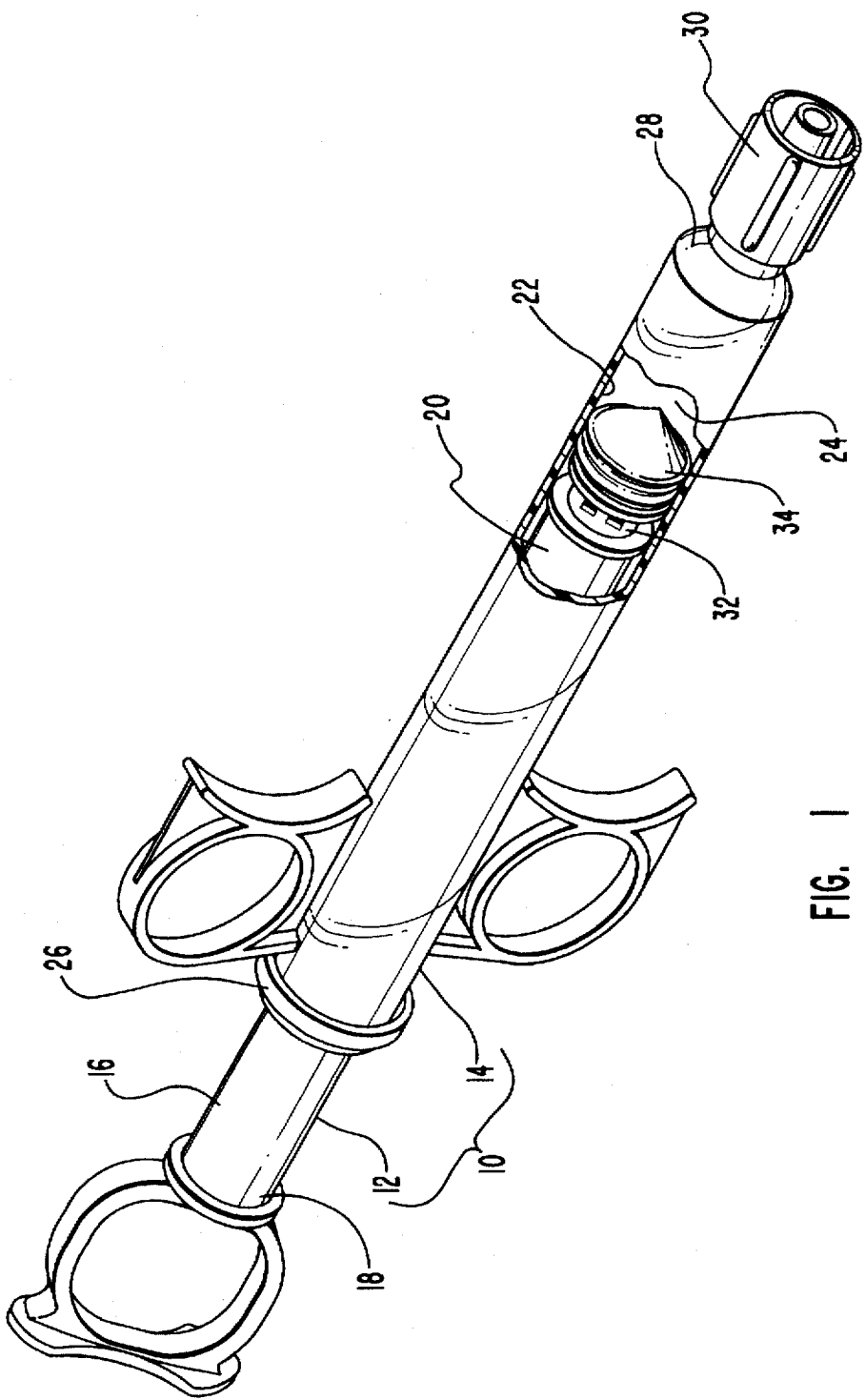
FIG. 1 is perspective view of a syringe with a portion of the syringe barrel cut-away, revealing a plunger with a sealing cap attached to the end thereof.

Depicted in FIG. 1 is a syringe 10 comprising a plunger 12 slidably received within a barrel 14. Plunger 12 is shown as having an exterior surface 16 extending between a proximal end 18 and a distal end 20. Barrel 14 is shown as comprising an interior surface 22 that defines a lumen 24 longitudinally extending through barrel 14. Barrel 14 is further shown as comprising an access end 26 through which plunger 12 is received within lumen 24, and an opposing discharge end 28 through which fluid is received within and discharged from lumen 24. In the embodiment shown, a luer lock connector 30 is rotatably attached to discharge end 28 for selective attachment to alternative medical devices. In alternative embodiments, various types of needles or adapters can be attached to discharge end 28 in fluid communication with lumen 24.

Positioned at distal end 20 of plunger 12 is a plunger tip 32 having a sealing cap 34 attached thereto. As better shown in FIG. 2, plunger tip 32 comprises an exterior surface 36 extending between a proximal end 38 and a distal end 40. Plunger tip 32 is further shown as comprising a substantially cylindrical portion 39 positioned at proximal end 38, a conical head 52 positioned at distal end 40, and an annular tapered portion 41 that extends therebetween.

Figure 2:
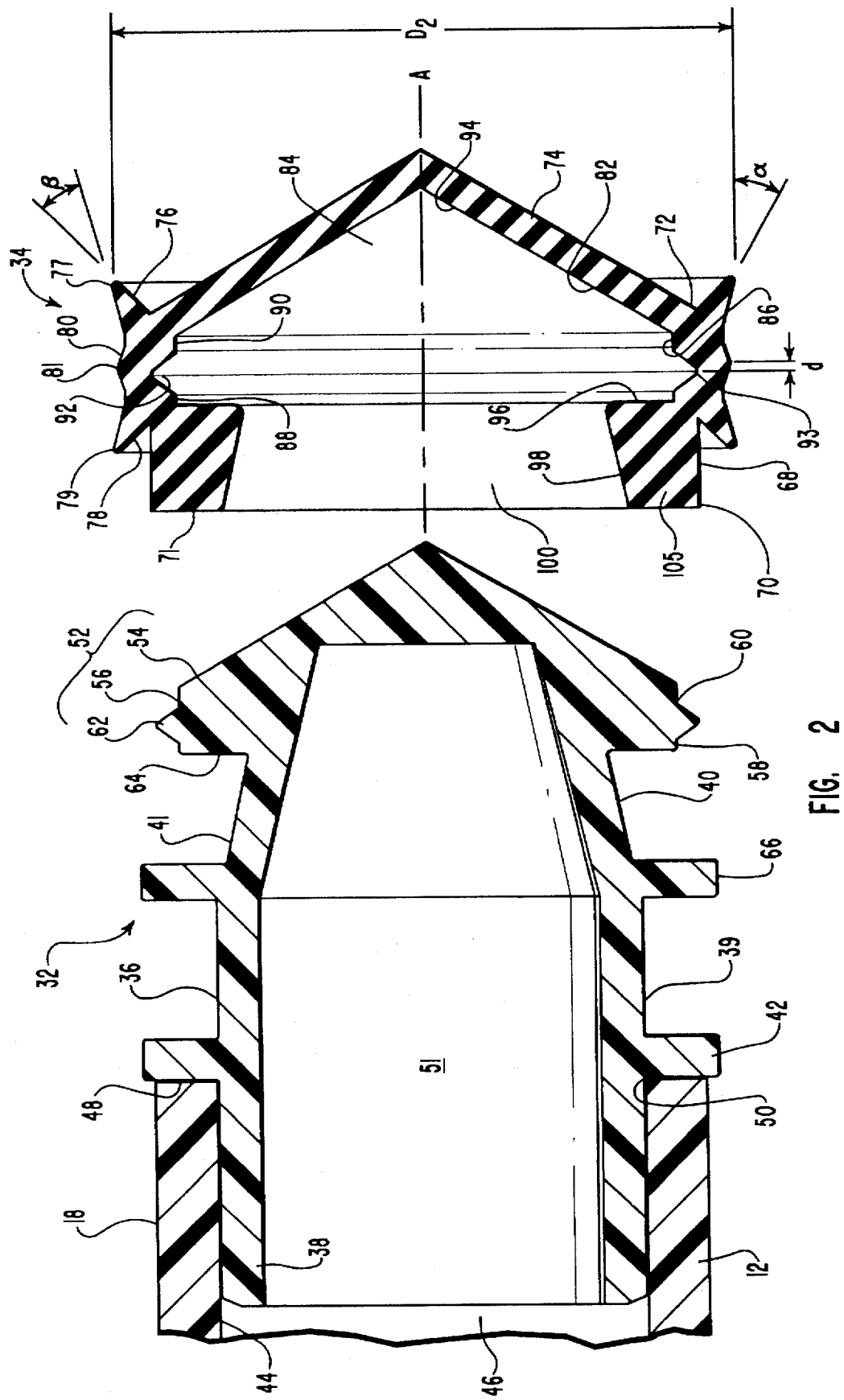
FIG. 2 is an enlarged, exploded cross-sectional view of the plunger tip and sealing cap of the plunger shown in FIG. 1.

Encircling and radially extending out from exterior surface 36 of cylindrical portion 39 is a first stop ridge 42. As also shown in FIG. 2, plunger 12 is shown as having an interior surface 44 defining a chamber 46. Proximal end 18 of plunger 12 is also shown as terminating at an annular end face 48 which defines an opening 50 to chamber 46. The inner diameter of interior surface 44 of plunger 12 is comparable to the outer diameter of proximal end 38 of plunger tip 32. As such, plunger tip 32 is mounted to plunger 12 by slidably receiving proximal end 38 of plunger tip 32 within opening 50 of chamber 46 until end face 48 abuts first stop ridge 42. An adhesive or other bonding means can be positioned between interior surface 44 and exterior surface 36 so as to provide a tight, sealed bond between plunger tip 32 and plunger 12.

In alternative embodiments, plunger tip 32 can be integrally molded on plunger 12. As such, plunger 12 need not be hollow but can be solid. In like manner, although plunger tip 32 is shown as having an internal chamber 51 to decrease material cost, plunger tip 32 can also be formed without chamber 51.

Conical head 52 is shown as comprising an annular distal end face 54 that radially slopes out in a proximal direction to an outside shoulder 56. Shoulder 56 has a proximal portion 58 and a distal portion 60. Encircling and radially extending out from between portions 58 and 60 is an annular tapered ridge 62. Conical head 52 further includes an annular proximal end face 64 that extends between proximal portion 58 of shoulder 56 and tapered portion 41. As will be discussed later in greater detail, an annular second stop ridge 66 encircles and radially projects out from exterior surface 36 between first stop ridge 42 and head 52.

Sealing cap 34 is shown as comprising an annular sidewall 68 extending between a proximal end 70 having an annular end face 71 and an opposing distal end 72. A conical crown 74 is integrally attached to sidewall 68 so as to cover distal end 72. An annular first sealing wing 76 encircles and radially projects outward in a distal direction from distal end 72. First sealing wing 76 tapers to an annular lip 77 at an angle β in a range between about 20° to about 40° with about 25° to about 35° being more preferred. First sealing wing 76 also projects at an inside angle α that is less than 90° relative to the longitudinal axis "A" of sealing cap 34. First sealing wing 76 typically projects at an angle in a range between about 20° to about 40°, and more preferably in a range from between about 25° to about 35° relative to longitudinal axis "A" of sealing cap 34.

An annular second sealing wing 78 encircles and radially projects out from sidewall 68 proximal of first sealing wing 76. Second sealing wing 78 tapers to an annular lip 79 at an angle comparable to angle β. Second sealing wing 78 projects in a proximal direction at an inside angle less than 90° relative to the longitudinal axis "A" of sealing cap 34. The angle at which second sealing wing 78 projects is comparable to the angle α at which first sealing wing 76 projects.

Positioned between first sealing wing 76 and second sealing wing 78 is a tapered, annular sealing ridge 80 which encircles and radially projects out from sidewall 68. Sealing ridge 80 tapers to an annular lip 81 that has an outer diameter that is preferably, although not necessarily, smaller than the outer diameter of the annular lips 77 and 79 when sealing wings 76 and 78 are in an unflexed position.

Sealing cap 34 is further shown as comprising an interior surface 82 defining a cavity 84. Cavity 84 is configured to complementarily receive head 52 of plunger tip 32. More specifically, interior surface 82 comprises an annular side face 86 which is adjacent to and substantially parallel to sidewall 68. Side face 86 includes a proximal shoulder 88 and a distal shoulder 90. Formed between shoulders 88 and 90 is a tapered side groove 92 that is recessed within side face 86. Side groove 92 tapers to an annular apex 93. In the preferred embodiment, apex 93 is positioned slightly proximal of annular lip 81 of sealing ridge 80 as designated by the distance "d". In alternative embodiments, apex 93 can be aligned with annular lip 81 or even distal of annular lip 81.

Formed distal of side face 86 is a conical inside surface 94 that is formed to complementarily abut distal end face 54 of head 52. Radially projecting inward from proximal shoulder 88 is an annular face 96. A frustoconical inside wall 98 extends between annular face 96 and annular end face 71, thereby defining an opening 100 to cavity 84. Inside wall 98 and annular face 96 define a retaining lip 105.

Figure 3:
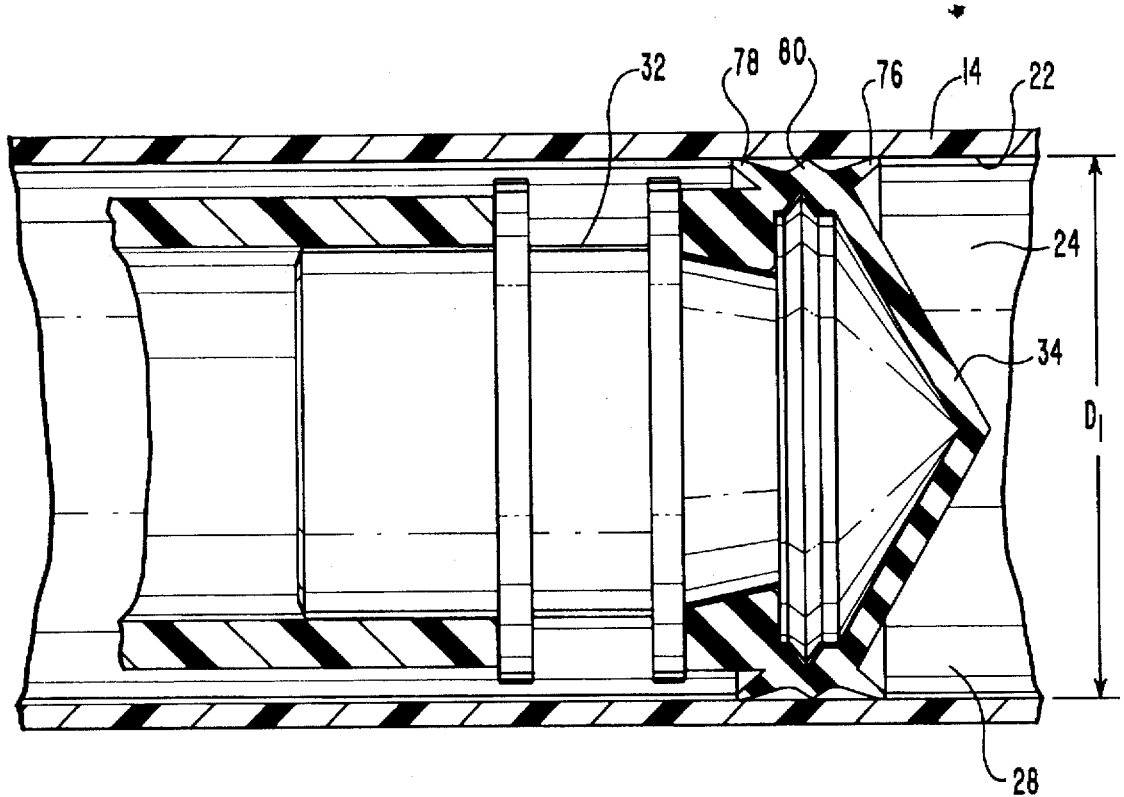
FIG. 3 is a partial cross-sectional view of the plunger tip received within the sealing cap of FIG. 2 and positioned within the barrel of a syringe.

Sealing cap 34 is preferably made of a resiliently flexible material such as silicone or rubber. Alternatively, other medical grade materials having comparable properties can be used. As a result of the resilient and flexible nature of sealing cap 34, opening 100 can be radially expanded to allow head 52 to be received within cavity 84, as shown in FIG. 3. As seen in FIG. 3 but as primarily noted by the reference characters in FIG. 2, cavity 84 is configured so that as distal end face 54 of head 52 abuts against conical face 94, tapered ridge 62 is received within side groove 92. Furthermore, proximal portion 58 and distal portion 60 of outside shoulder 56 are aligned against proximal shoulder 88 and distal shoulder 90, respectively, of sealing cap 34.

Once head 52 is positioned within cavity 84, inside wall 98 resiliently returns to its original relaxed or at-rest shape, such that annular face 96 is aligned against proximal end face 64 of head 52 and annular end face 71 of sealing cap 34 is biased against second stop ridge 66. As a result, sealing cap 34 is securely held on plunger tip 32. Sealing cap 34 is preferably sized so as to be unstressed once received on head 52. A slight gap may even exist between sealing cap 34 and head 52.

Sealing cap 34 can be manufactured from a variety of conventional manufacturing processes. By way of example and not be limitation, sealing cap 34 can be manufactured by transfer molding or liquid injection molding. Furthermore, sealing cap 34 can be coated with a medical grade lubricant such as a silicone oil. In an alternative embodiment, sealing cap 34 can be coated with a fluorosilicon fluid. The fluorosilicon fluid is marketed as an improved lubricant since it does not soften the silicone material.

FIG. 3 illustrates sealing cap 34 mounted on plunger tip 32 and the combination thereof being received within lumen 24 of barrel 14 at ambient conditions. As used in the specification and the appended claims, the term "ambient conditions" is defined as meaning that no external force is being applied to the proximal end of plunger 12 and, therefore, no internal pressure is being generated within lumen 24 of barrel 14. The inner diameter $D_1$ of barrel 14 (see FIG. 3) is slightly smaller than the outer diameter $D_2$ of first sealing wing 76 and second sealing wing 78 (see FIG. 2) when sealing wings 76 and 78 are in an unflexed condition. Accordingly, as sealing cap 34 is positioned within lumen 24 of barrel 14, sealing wings 76 and 78 radially flex inward creating a continuous and positive bias between sealing wings 76 and 78 and interior surface 22 of barrel 14. As a result of the positive bias, a seal is formed between sealing wings 76 and 78 and interior surface 22 of barrel 14 at ambient conditions.

Although annular lip 81 of sealing ridge 80 is shown in FIG. 3 as slightly touching interior surface 22 of barrel 14, this is not necessary. In alternative embodiments, sealing ridge 80 may be separated from interior surface 22 when no pressure is being exerted on sealing cap 34.

As a result of the minimal surface contact and the low bias force between sealing wings 76 and 78 and interior surface 22, there is relatively low friction between sealing cap 34 and barrel 14. As a result, syringe 10 minimizes stiction at low pressures within barrel 14 and is highly effective in delivering micro amounts of medication. Furthermore, syringe 10 is highly sensitive to variations of fluid pressures within lumen 22 at low pressure ranges.

Figure 4:
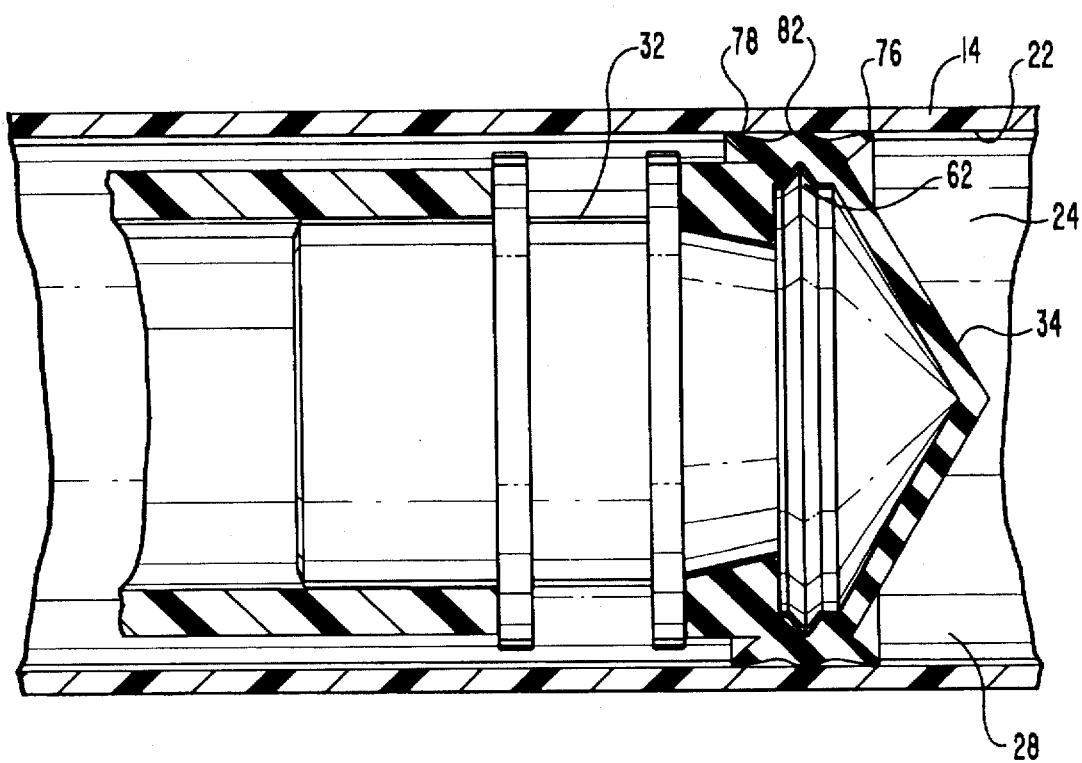
FIG. 4 is a partial cross-sectional view of the plunger tip and sealing cap shown in FIG. 3 wherein a sealing means attached to the sealing cap is urged against the interior of the barrel under increased pressure within the barrel.

Depicted in FIG. 4 is the syringe assembly of FIG. 3 wherein the sealing cap 34 is under an increased pressure. That is, with the application of an external force to the proximal end of plunger 12, plunger 12 has been advanced so as to compress a fluid within discharge end 28 of barrel 14, thereby generating a positive internal pressure within the discharge end 28 of barrel 14. In ram, the fluid produces a corresponding compressive force against sealing cap 34. As the pressure gradually increases against sealing cap 34, several structural modifications of sealing cap 34 gradually transpire. Initially, as the pressure increases, first sealing wing 76 flexes radially outward with an increased force so as to produce an increase in the effective seal between sealing wing 76 and interior surface 22 of barrel 14.

Furthermore, since sealing cap 34 is made of a flexible material, sealing cap 34 in part reacts as a fluid. Accordingly, as the pressure against sealing cap 34 increases, the material of sealing cap 34 attempts to flow toward the low pressure zone which is located proximal of sealing cap 34. As the material of sealing cap 34 begins to flow around tapered ridge 62, the material is pushed radially outward causing sealing ridge 80 to complementarily radially project outward so as to bias against interior surface 22 of barrel 14. Furthermore, by positioning tapered ridge 62 proximal of sealing ridge 80, tapered ridge 62 is better able to direct more of the material of sealing cap 34 against sealing ridge 80. As a result, sealing ridge 80 creates a second seal that incrementally increases in effectiveness as the pressure within barrel 14 increases.

Although the effective increase in sealing also results in an increase of frictional forces, the resulting detriment of having an increase in friction is decreased as the pressure within barrel 14 increases. That is, the need for dispensing micro amounts of medication or sensing the variance in pressure of a fluid within barrel 14 is decreased as the pressure within barrel 14 increases.

As the pressure within barrel 14 begins to decrease, the resilient nature of sealing cap 34 causes sealing cap 34 to return to its original configuration, as shown in FIG. 3. As a result of the above-described configuration, syringe 10 has low friction at low pressure and increased sealing effectiveness as the pressure increases. The variable properties of inventive syringe 10 thus enables it to be used in a variety of different applications.

Second sealing wing 78 is of greatest effectiveness when syringe 10 is used in aspiration. That is, as syringe plunger 12 is retracted within barrel 14, a negative pressure can be created distal of sealing cap 34. As used in the specification and the appended claims, the term "negative pressure" is defined as meaning a pressure less than the ambient pressure. In the embodiment as shown in FIG. 3, as the negative pressure is created, second sealing wing 78 radially flexes outward so as to increase the bias against interior surface 22. As such, the greater the negative pressure, the greater the seal produced between second sealing wing 78 and interior surface 22. Further, the adjacent positioning of tapered ridge 62 acts as a support for second sealing wing 78, thereby preventing second sealing wing 78 from folding back over on itself.

Using the above teachings in the formation of syringe 10, syringe 10 can be constructed so as to provide an effective seal between sealing cap 34 and interior surface 22 of barrel 14 that will not leak when exposed to pressures greater than about 200 pounds per square inch, and preferably greater than about 400 pounds per square inch, and more preferably greater than about 600 pounds per square inch. Likewise, an effective seal between sealing cap 34 and interior surface 22 can be made that will prevent leaking against significant negative pressures.

Using the above teachings, it is also possible to design syringes that can work over a broad spectrum of desired pressures or that can be specifically designed to operate within a desired range of pressures. For example, where it is desirable that the inventive syringe only be operated under high pressures, it may be desirable to have sealing wings 76 and 78 project at a steeper angle so that a greater initial biasing force is produced between sealing wings 76 and 78 and interior surface 22. Alternatively, sealing ridge 80 could be increased in size so as to engage interior surface 22 at lower pressures, or even under ambient conditions, and with greater force. Based on the teachings disclosed herein, those skilled in the art will be able to adjust the size and configuration of the various elements of the present invention to obtain desired properties for both different sizes and different kinds of syringes.

The present invention also provides primary sealing means formed on sealing cap 34 for producing a continuous sealing engagement between sealing cap 34 and interior surface 22 of barrel 14. By way of example and not by limitation, the primary sealing means includes first sealing wing 76, as discussed above. First sealing wing 76 is disclosed as having an outer diameter that is smaller than the inner diameter of lumen 24. As such, first sealing wing 76 biases against interior surface 22 so as to produce a continuous sealing engagement therewith. In an alternative embodiment, the primary sealing means can include conventional structures used in sealing a conventional plunger against the interior surface of a syringe barrel. For example, the primary sealing means can comprise an annular gasket which encircles and radially extends out from sealing cap 34 to engage interior surface 22 of barrel 14. Such an annular gasket need not radially urge out under increased pressure but can be used to maintain a constant seal.

Furthermore, the present invention provides variable sealing means for producing a sealing engagement between a portion of sidewall 68 and interior surface 22 of barrel 14 that increases in sealing effectiveness as plunger 12 advances within barrel 14 so as to increase the pressure within barrel 14. By way of example and not by limitation, the variable sealing means includes sealing ridge 80 that radially projects out from sidewall 68 and tapered ridge 62 that radially projects out from shoulder 56. As discussed above, ridge 62 is received within side groove 92 which in mm is positioned adjacent to sealing ridge 80. Accordingly, as plunger 12 advances within barrel 14 so as to increase the pressure within barrel 14, sealing ridge 80 is urged radially outward to producing a sealing engagement with interior surface 22 of barrel 14.

The present invention also comprises engagement means, responsive to pressure generated within the syringe barrel, for increasing the force with which the annular sealing ridge engages the interior surface of the syringe barrel in proportion to the pressure generated within the syringe barrel. In the preferred embodiment illustrated in FIGS. 1–4, the engaging means comprises the conical head 52 in combination with the complementary surfaces of cavity 84. As set forth above, when a positive pressure is generated within barrel 14, the sloping surfaces of conical head 52 cooperate with the complementary sloping surfaces within cavity 84 to cause sealing cap 34 to compress or flex, thereby increasing the force with which sealing wing 76 and sealing ridge 80 engage the interior surface 22 of barrel 14. Similarly, when a negative pressure or partial vacuum is generated within barrel 14, the sloping surfaces of conical head 52 cooperate with the complementary sloping surfaces within cavity 84 to cause sealing cap 34 to compress or flex, thereby increasing the force with which sealing wing 78 and sealing ridge 80 engage the interior surface 22 of barrel 14. The force with which the respective sealing members engage the interior surface 22 of barrel 14 is proportional to, and automatically increases in response to, any increase in pressure (either positive or negative) generated within barrel 14.

Figure 5A:
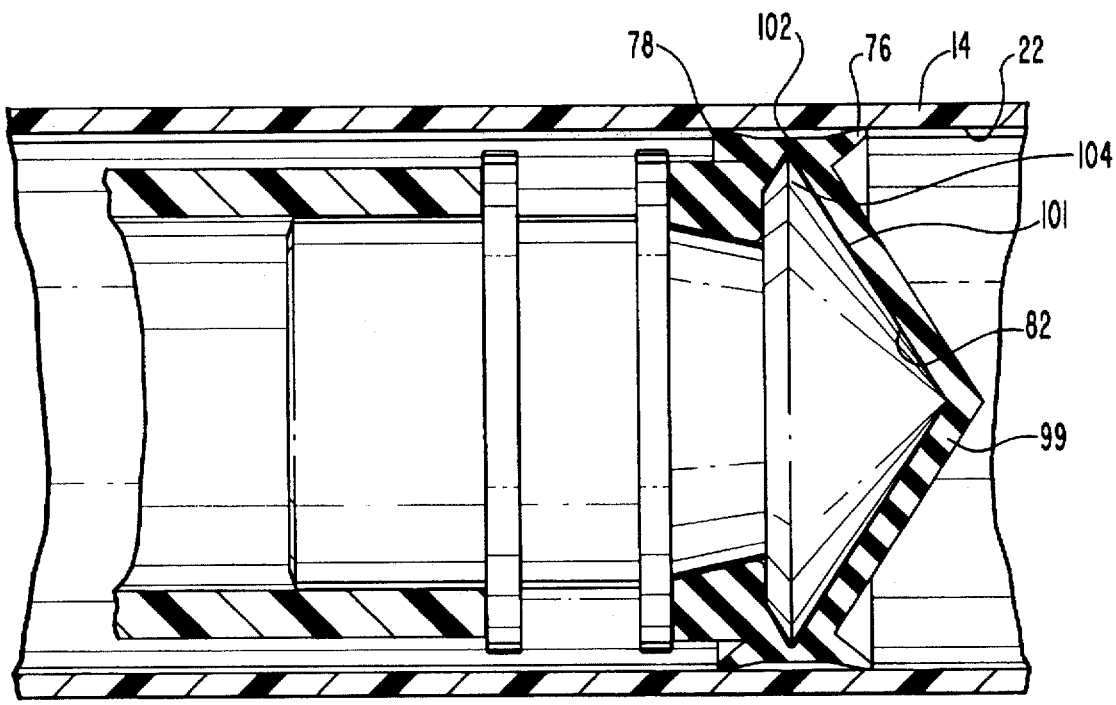
FIG. 5A is a partial cross-sectional view of an alternative embodiment of a plunger tip and sealing cap for producing a seal against the interior surface of the barrel.
Figure 5B:
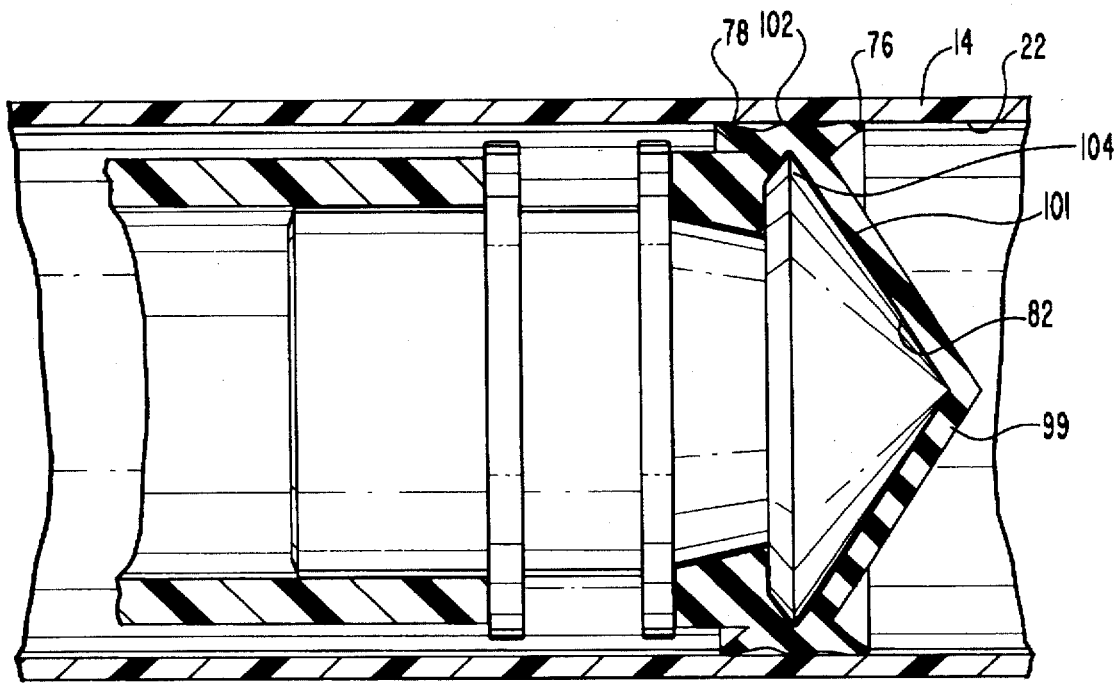
FIG. 5B is a partial cross-sectional view of the plunger tip and sealing cap in FIG. 5A wherein a sealing means attached to the sealing cap is urged against the interior surface of the barrel under increased pressure within the barrel.

An alternative embodiment of the variable sealing means is disclosed in FIG. 5A. As shown therein, a sealing cap 99 is provided having first sealing wing 76 and second sealing wing 78 comparable to sealing cap 34. In contrast, however, sealing cap 99 does not include annular sealing ridge 80 projecting between sealing wings 76 and 78. Rather, a recessed portion 102 is formed between sealing wings 78 and 80. Furthermore, a conical head 101 is shown as having a distal end face 103 that uniformly slopes to an annular outside edge 104. Interior surface 82 of sealing cap 99 is designed to complementarily receive head 101. Outside edge 104 is positioned sufficiently close to recessed portion 102 that as pressure is applied to sealing cap 99, outside edge 104 causes the flow of the material of sealing cap 99 to push a portion of recessed portion 102 radially outward, as shown in FIG. 5B, so as to bias and seal against interior surface 22 of barrel 14.

It is evident that the ability of recessed portion 102 to effectively seal against interior surface 22 of barrel 14 is dependent on the distance between recessed portion 102 and interior surface 22 and the distance between outside edge 104 and recessed portion 102. Such distances, however, are not fixed but must be determined based on the size of the syringe and the amount of pressure that is desired to be withstood. For example, as the size of sealing cap 99 increases, the amount of material capable of flowing also increases. As such, outside edge 104 can be positioned farther away from interior surface 22 of barrel 14.

Figure 6A:
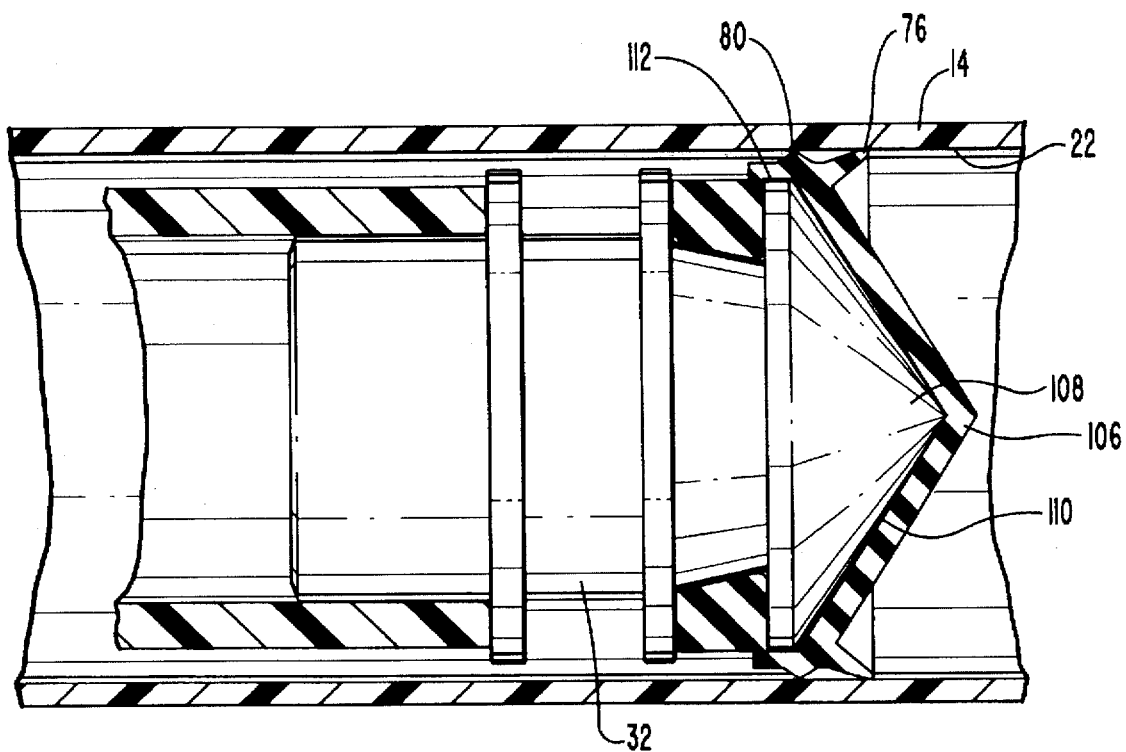
FIG. 6A is a partial cross-sectional view of an alternative embodiment of a plunger tip and sealing cap for producing a seal against the interior surface of a syringe barrel.
Figure 6B:
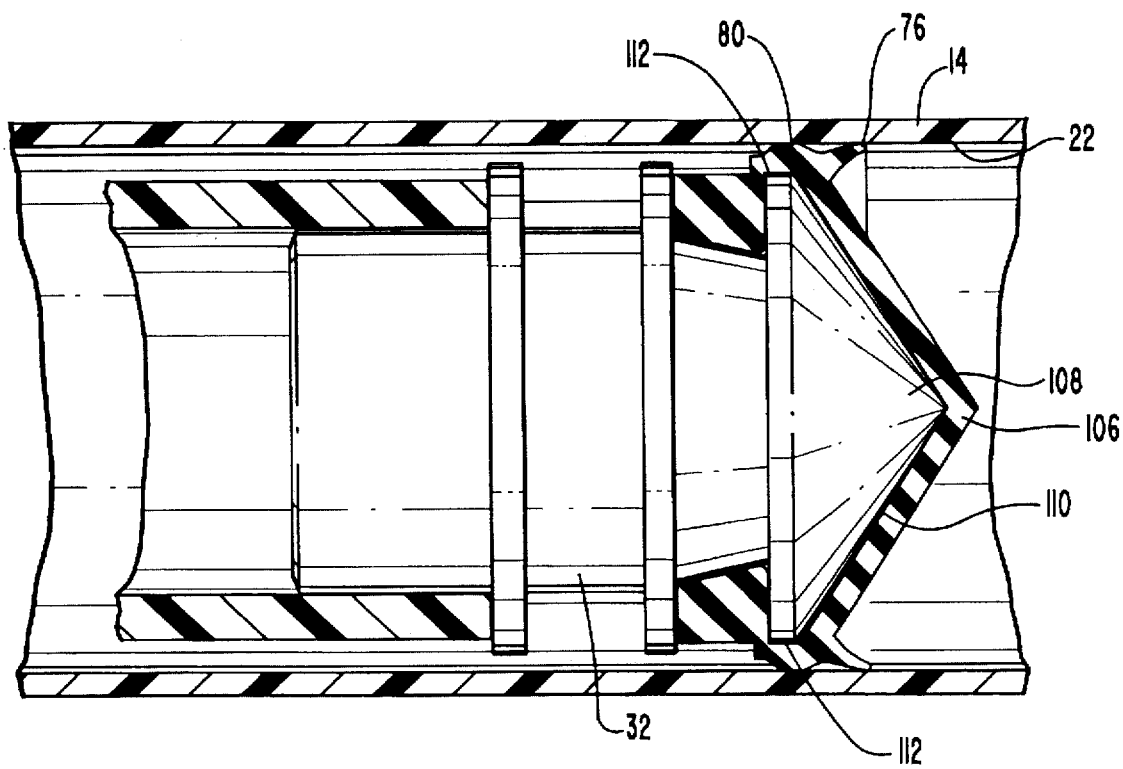
FIG. 6B is a partial cross-sectional view of the plunger tip and sealing cap in FIG. 6A wherein a sealing means attached to the sealing cap is urged against the interior surface of the barrel under increased pressure within the barrel.

FIGS. 6A and 6B disclose another alternative embodiment of the inventive aspect of the present invention. As disclosed therein, a sealing cap 106 can be formed with first sealing wing 76, annular sealing ridge 80, but excluding second sealing wing 78. Furthermore, a conical head 108 is disclosed comprising a conical distal end face 110 that uniformly and radially slopes out to an annular outside shoulder 112. Shoulder 112 is shown as being substantially parallel with the longitudinal axis of plunger tip 32. Such an embodiment functions under positive pressure in substantially the same way as discussed above with regard to FIG. 3. That is, as shown in FIG. 6B, as the pressure increases against sealing cap 106, first sealing wing 76 flexes to bias against interior surface 22 and sealing ridge 80 radially projects out to sealing engage interior surface 22. Furthermore, even though second sealing wing 78 is removed, sealing cap 34 still functions as a seal under low negative pressure during aspiration.

Figure 7A:
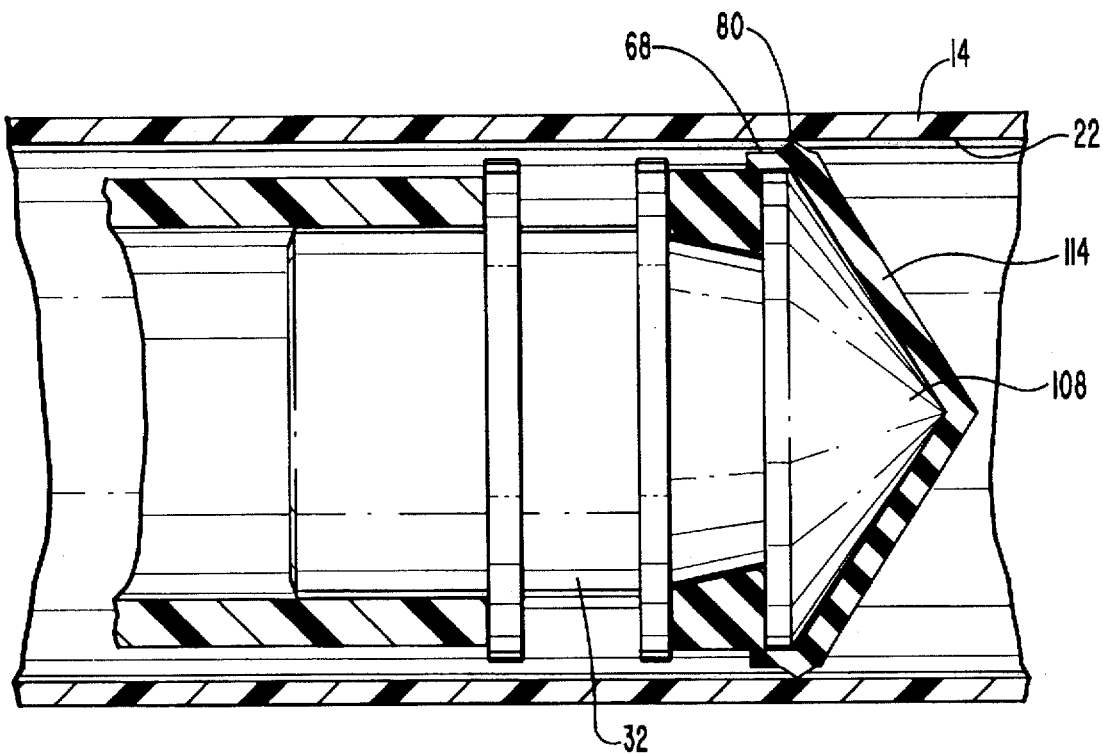
FIG. 7A is a partial cross-sectional view of an alternative embodiment of a plunger tip and sealing cap, the sealing cap having an annular sealing ridge for producing a seal against the interior surface of a syringe barrel.
Figure 7B:
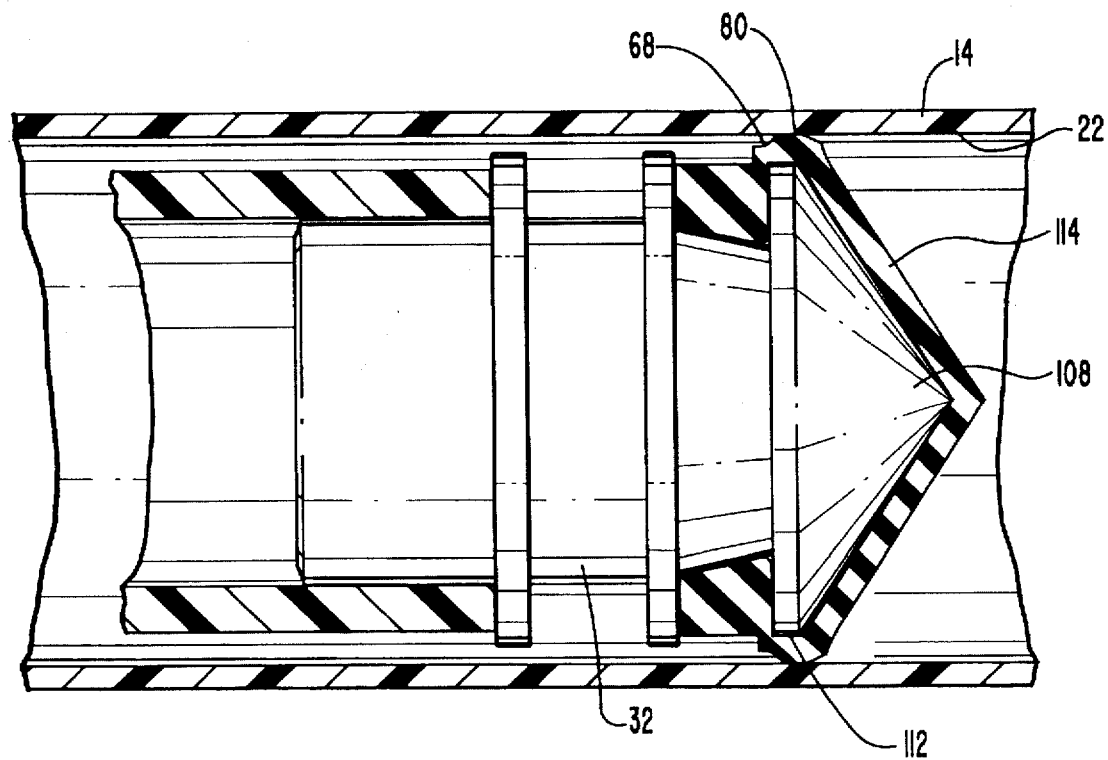
FIG. 7B is a partial cross-sectional view of the plunger tip and sealing cap in FIG. 7A wherein the sealing ridge attached to the sealing cap is urged against the interior surface of the barrel under increased pressure within the barrel.

Finally, FIG. 7A and 7B disclose yet another alternative embodiment of an inventive aspect of the present invention. As disclosed therein, a sealing cap 114 is formed comparable to sealing cap 106 except that first sealing wing 76 has been removed. As such, sealing cap 114 comprises annular sidewall 68 on which annular sealing ridge 80 solitarily encircles and radially extends therefrom. In this embodiment, however, it is desired that sealing ridge 80 have an outer diameter sufficiently large to initially engage interior surface 22 of barrel 14 under ambient conditions. This is because annular sealing ridge 80 is the sole structure for producing a seal between sealing cap 114 and barrel 14. As depicted in FIG. 7B, as the pressure increases within barrel 14 the material of sealing cap 114 begins to flow so that outside edge 112 of head 108 radially pushes sealing ridge 80 against interior surface 22, thereby effectively increasing the seal.

The present invention may be embodied in other specific forms without departing from its spirit or essential characteristics. The described embodiments are to be considered in all respects only as illustrated and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A syringe plunger tip adapted to provide enhanced sealing engagement between the plunger tip and the interior surface of a syringe barrel at high pressures, the plunger tip comprising:

cap means for effecting sealing engagement with the interior surface of said syringe barrel so as to provide enhanced sealing at high pressures to prevent fluid leakage around the cap means;

head means for receiving said cap means in mating engagement, said head means and said cap means providing in combination the plunger tip;

wherein said cap means comprises variable sealing means formed at said radial periphery of said cap means so as to provide a sealing contact with the interior of the syringe barrel that increases with increasing pressure exerted against said plunger tip; and wherein said head means comprises engagement means positioned in said cap means for radially directing the pressure exerted on said cap means as the pressure increases so as to urge the variable sealing means into tighter engagement with the interior surface of the syringe barrel.

2. A syringe plunger tip as recited in claim 1, wherein the variable sealing means comprises a sealing cap including an annular sidewall, an annular sealing ridge encircling and radially projecting out from the sidewall, and an interior surface defining a cavity within the sealing cap, the cavity having an annular side groove configured to complementary receive an outer edge of the head means of the plunger tip, the side groove being positioned relative to the annular sealing ridge so that the annular sealing ridge radially urges out to increasingly engage the interior surface of the barrel as the plunger till is advanced within the barrel to increase the pressure within the barrel.

3. A syringe plunger tip as recited in claim 2, further comprising primary sealing means for producing a continuous sealing engagement between the sealing cap and the interior surface of the barrel, the primary sealing means being formed on the sealing cap distal to the annular sealing ridge.

4. A syringe plunger tip as recited in claim 3, wherein the primary sealing means comprises an annular first sealing wing encircling and radially projecting outward in a distal direction from an exterior surface of the annular sidewall at an angle less than 90° relative to the longitudinal axis of the sealing cap, the first sealing wing being positioned distal to the annular sealing ridge and contacting the interior surface of the syringe barrel when the sealing cap attached to the head of the plunger tip is received within the syringe barrel.

5. A syringe plunger tip as recited in claim 4, wherein the annular first sealing wing projects at an angle in a range between about 20° to about 40° relative to the longitudinal axis of the sealing cap.

6. A syringe plunger tip as recited in claim 2, wherein the side groove on the interior surface of the sealing cap is aligned proximal of the annular sealing ridge.

7. A syringe plunger tip as recited in claim 2, further comprising an annular second sealing wing encircling and radially projecting outward in a proximal direction from an exterior surface of the annular sidewall at an angle less than 90° relative to the longitudinal axis of the sealing cap, the second sealing wing being positioned proximal to the annular sealing ridge and contacting the interior surface of the syringe barrel when the sealing cap attached to the head of the plunger till is received within the syringe barrel.

8. A syringe plunger tip as recited in claim 7, wherein the annular second sealing wing projects at an angle in a range between about 20° to about 40° relative to the longitudinal axis of the sealing cap.

9. A syringe plunger tip as recited in claim 2, wherein the sealing cap includes a crown mounted on the annular sidewall having a conical configuration.

10. A syringe plunger tip as recited in claim 9, wherein the interior surface of the sealing cap includes a conical face adjacent to the crown.

11. A syringe plunger tip as recited in claim 2, wherein the head means includes a head of a plunger, wherein the interior surface of the sealing cap defining the cavity within the sealing cap is configured to complementary receive the head of the plunger, wherein the cavity includes an annular side face adjacent to and substantially parallel to an exterior surface of the annular sidewall, the side groove being tapered and recessed within the side face.

12. A syringe plunger tip as recited in claim 1, wherein the cap means includes a sealing cap made of silicone.

13. A syringe plunger tip as recited in claim 1, wherein the cap means includes a sealing cap made of rubber.

14. A syringe plunger tip as recited in claim 1, wherein the cap means includes a sealing cap coated with a lubricant.

15. A syringe plunger tip as recited in claim 4, wherein first sealing wing has an outer diameter and the sealing ridge has an outer diameter, the outer diameter of the first sealing wing being greater than the outer diameter of the sealing ridge when the sealing cap is positioned outside of the barrel.

16. A sealing cap for attachment to the head of a syringe plunger to enable a sealing engagement between the sealing cap and the interior surface of a syringe barrel, the head of the plunger radially sloping outward to an annular outer edge, the sealing cap comprising:

(a) an annular sidewall having an exterior surface extending between a proximal end and a distal end;

(b) a crown mounted to the sidewall so as to cover the distal end of the sealing cap;

(c) an annular first sealing wing encircling and radially projecting outward in a distal direction from the exterior surface of the sidewall at an angle less than 90° relative to the longitudinal axis of the sealing cap, the first sealing wing contacting the interior surface of the barrel when the sealing cap attached to the head of the plunger is received within the barrel;

(d) an interior surface defining a cavity within the sealing cap, the interior surface being configured to complementary receive the head of the plunger, the cavity including an annular side face adjacent to and substantially parallel to the exterior surface of the sidewall, the interior surface further including an annular tapered groove recessed within the annular face, the groove being positioned relative to the sidewall so that a portion of the sidewall proximal of the first sealing wing is urged against the interior surface of barrel as pressure is increased within the barrel distal of the sealing cap; and (e) an end face positioned at the proximal end of the sidewall and defining an opening to the cavity through which the head of the plunger is received within the cavity of the sealing cap.

17. A sealing cap as recited in claim 16, wherein the annular first sealing wing projects at an angle in a range between about 20° to about 40° relative to the longitudinal axis of the sealing cap.

18. A sealing cap as recited in claim 16, further comprising an annular second sealing wing encircling and radially projecting outward in a proximal direction from the exterior surface of the sidewall at an angle less than 90° relative to the longitudinal axis of the sealing cap, the second sealing wing being positioned proximal of the first sealing wing and contacting the interior surface of the barrel when the sealing cap attached to the head of the plunger is received within the barrel.

19. A sealing cap as recited in claim 16, wherein the portion of the sidewall that urges against the interior surface of the barrel comprises an annular sealing ridge encircling and radially projecting out from the sidewall.

20. A sealing cap as recited in claim 16, wherein the sealing cap is made of silicone.

21. A sealing cap as recited in claim 16, wherein the crown has a conical configuration.

22. A sealing cap for attachment to the head of a syringe plunger to enable a sealing engagement between the sealing cap and the interior surface of a syringe barrel, the head of the plunger radially sloping outward to an annular outer edge, the sealing cap comprising:

(a) an annular sidewall having an exterior surface extending between a proximal end and a distal end;

(b) a conical crown mounted on the annular sidewall so as to cover the distal end of the sealing cap;

(c) an annular first sealing wing encircling and radially projecting outward in a distal direction from the exterior surface of the sidewall at an angle less than 90° relative to the longitudinal axis of the sealing cap, the first sealing wing contacting the interior surface of the barrel when the sealing cap attached to the head of the plunger is received within the barrel;

(d) an annular second sealing wing encircling and radially projecting outward in a proximal direction from the exterior surface of the sidewall at an angle less than 90° relative to the longitudinal axis of the sealing cap, the second sealing wing being positioned proximal of the first sealing wing and contacting the interior surface of the barrel when the sealing cap attached to the head of the plunger is received within the barrel;

(e) an annular sealing ridge encircling and radially projecting out from the exterior surface of the sidewall between the fist sealing wing and the second sealing wing;

(f) an interior surface defining a cavity within the sealing cap, the cavity being configured to complementary receive the head of the plunger, the cavity including an annular side groove configured to complementary receive the outer edge of the head of the plunger, the side groove being positioned relative to the annular sealing ridge so that the annular, sealing ridge radially urges out to increasingly engage the interior surface of the barrel as the plunger is advanced within the barrel to increase the pressure within the barrel; and (g) an end face positioned at the proximal end of the sealing cap and defining an opening to the cavity through which the head of the plunger is received within the cavity of the sealing cap.

23. A sealing cap as recited in claim 22, wherein the first sealing wing and the second sealing wing each project at an angle in a range between about 20° to about 40° relative to the longitudinal axis of the sealing cap.

24. A sealing cap as recited in claim 22, wherein the sealing cap further includes an annular retaining lip positioned at the proximal end of the sealing cap to hold the sealing cap on the plunger head.

25. A sealing cap as recited in claim 22, wherein the sealing cap is made of silicone.

26. A sealing cap as recited in claim 22, wherein the interior surface of the cavity is configured to complementary receive the head of the plunger, the cavity including an annular side face adjacent to and substantially parallel to the exterior surface of the sidewall, the side groove being tapered and recessed within the annular side face.

27. A sealing cap as recited in claim 22, wherein the first sealing wing, the second sealing wing, and the sealing ridge each have an outer diameter, the outer diameter of the first sealing wing and the second sealing wing being greater than the outer diameter of the sealing ridge when the sealing cap is positioned outside of the barrel.

28. A sealing cap as recited in claim 22, wherein the side groove on the interior surface of the barrel is aligned proximal of the annular sealing ridge.

29. A syringe having an improved plunger tip adapted to provide enhanced sealing engagement between the plunger tip and an interior surface of a syringe barrel over a range of pressures characterized by (i) low pressures requiring low friction so as to enhance sensitivity to pressure changes exerted on the syringe plunger and so as to reduce friction of the syringe plunger at low pressures, and characterized by (ii) high pressures requiring enhanced sealing to prevent fluid leakage around the sealing cap, the syringe comprising:

(a) a barrel having an interior surface defining a lumen longitudinally extending through the barrel;

(b) an elongated plunger slidably received within the lumen of the barrel; and (c) a plunger tip comprising in combination a head positioned at one end of said plunger and a flexible sealing cap mounted on the head of the plunger, the sealing cap having a radial periphery that engages the interior surface of the barrel, and said sealing cap comprising:

i. primary sealing means formed on the sealing cap at said radial periphery thereof so as to provide a low friction sealing contact with the interior surface of the syringe barrel at low pressures of the pressure range; and ii. variable sealing means formed at said radial periphery of said sealing cap so as to provide a second sealing contact with the interior of the syringe barrel that increases with increasing pressure exerted against said plunger tip, wherein said head comprises engagement means positioned in said sealing cap for radially directing the pressure exerted on said sealing cap as the pressure increases so as to urge the variable sealing means into tighter engagement with the interior surface of the syringe barrel.

30. A syringe as recited in claim 29, wherein the primary sealing means comprises an annular first sealing wing projecting radially outward in a distal direction from the radial periphery of the sealing cap at an angle less than 90° relative to the longitudinal axis of the sealing cap, the first sealing wing contacting the interior surface of the syringe barrel.

31. A syringe as recited in claim 29, further comprising an annular second sealing wing encircling and radially projecting outward in a proximal direction from the radial periphery of the sealing cap at an angle less than 90° relative to the longitudinal axis of the sealing cap, the second sealing wing being positioned proximal to the variable sealing means and contacting the interior surface of the barrel when the sealing cap mounted on the head of the plunger is received within the barrel.

32. A syringe as recited in claim 30, wherein the first sealing wing projects at an angle in a range between about 20° to about 40° relative to the longitudinal axis of the sealing cap.

33. A syringe as recited in claim 29, wherein the sealing cap includes a crown having a conical configuration.

34. A syringe as recited in claim 29, wherein the variable sealing means comprises:

(a) the head of the plunger having a conical configuration that radially slopes outward to an annular outer edge; and (b) an annular side groove disposed on an interior surface of the sealing cap and configured to complementary receive the outer edge of the head of the plunger, the side groove being positioned relative to an annular sidewall of the sealing cap so that the annular sidewall is urged radially outward to increasingly engage the interior surface of the barrel as the plunger is advanced within the barrel to increase the pressure within the barrel.

35. A syringe as recited in claim 29, wherein the variable sealing means comprises:

(a) the head of the plunger having a conical configuration that radially slopes outward to an annular outer edge;

(b) an annular sealing ridge encircling and radially projecting out from the radial periphery of the sealing cap proximal to the primary sealing means; and (c) an annular side groove disposed on an interior surface of the sealing cap and configured to complementary receive the outer edge of the head of the plunger, the side groove being positioned relative to the annular sealing ridge so that the annular sealing ridge is urged radially outward to increasingly engage the interior surface of the barrel as the plunger is advanced within the barrel to increase the pressure within the barrel.

36. A syringe as recited in claim 35, wherein the side groove on the interior surface of the sealing cap is aligned proximal to the annular sealing ridge.

37. A syringe for dispensing a fluid, the syringe comprising:

(a) a barrel having an interior surface defining a lumen longitudinally extending through the barrel;

(b) an elongated plunger having a distal end slidably receivable within the lumen of the barrel, the plunger further comprising a conical head positioned at the distal end of the plunger, the conical head radially sloping outward to an annular outer edge;

(c) a flexible sealing cap mounted on the head of the plunger, the sealing cap comprising:

(i) an annular sidewall having an exterior surface extending between a proximal end and a distal end;

(ii) a crown mounted on the annular sidewall so as to cover the distal end of the sealing cap;

(iii) an annular sealing ridge encircling and radially projecting out from the sidewall;

(iv) an interior surface defining a cavity within the sealing cap, the cavity having an annular side groove configured to complementary receive the outer edge of the head of the plunger, the side groove being positioned relative to the annular sealing ridge so that the annular sealing ridge radially urges out to increasingly engage the interior surface of the barrel as the plunger is advanced within the barrel to increase the pressure within the barrel; and (v) a end face positioned at the proximal end of the sealing cap and defining an opening to the cavity through which the head of the plunger is received within the cavity of the sealing cap.

38. A syringe as recited in claim 37, further comprising primary sealing means formed on the sealing cap distal of the annular sealing ridge for producing a continuous sealing engagement between the sealing cap and the interior surface of the barrel.

39. A syringe as recited in claim 38, wherein the primary sealing means comprises an annular first sealing wing encircling and radially projecting outward in a distal direction from the exterior surface of the sidewall at an angle less than 90° relative to the longitudinal axis of the sealing cap, the first sealing wing contacting the interior surface of the barrel when the distal end of the plunger is received within the barrel.

40. A syringe as recited in claim 37, further comprising an annular second sealing wing encircling and radially projecting outward in a proximal direction from the exterior surface of the sidewall at an angle less than 90° relative to the longitudinal axis of the sealing cap, the second sealing wing being positioned proximal of the annular sealing ridge and contacting the interior surface of the barrel when the sealing cap attached to the head of the plunger is received within the barrel.

41. A syringe as recited in claim 39, wherein the first sealing wing projects at an angle in a range between about 20° to about 40° relative to the longitudinal axis of the sealing cap.

42. A syringe as recited in claim 37, wherein the crown of the sealing cap has a conical configuration.

43. A syringe as recited in claim 37, wherein the side groove on the interior surface of the barrel is aligned proximal of the annular sealing ridge.

44. A syringe as recited in claim 37, wherein the interior surface of the cavity is configured to complementary receive the head of the plunger, the cavity including an annular side face adjacent to and substantially parallel to the exterior surface of the sidewall, the side groove being tapered and recessed within the side face.

45. A syringe as recited in claim 37, wherein the sealing cap is made of silicone.

46. A syringe as recited in claim 37, wherein the sealing cap is coated with a lubricant.

47. A syringe as recited in claim 37, wherein first sealing wing has an outer diameter and the sealing ridge has an outer diameter, the outer diameter of the first sealing wing being greater than the outer diameter of the sealing ridge when the sealing cap is positioned outside of the barrel.

48. A syringe for dispensing a fluid, the syringe comprising:

(a) a barrel having an interior surface defining a lumen longitudinally extending through the barrel;

(b) an elongated plunger having a distal end slidably received within the lumen of the barrel, the plunger further comprising a conical head positioned at the distal end of the plunger, the conical head radially sloping outward to a sharp annular outer edge;

(c) a flexible sealing cap mounted on the head of the plunger, the sealing cap comprising:

(i) an annular sidewall having an exterior surface extending between a proximal end and a distal end;

(ii) a conical crown mounted on the annular sidewall so as to cover the distal end of the sealing cap;

(iii) an annular first sealing wing encircling and radially projecting outward in a distal direction from the exterior surface of the sidewall at an angle less than 90° relative to the longitudinal axis of the sealing cap, the first sealing wing contacting the interior surface of the barrel when the distal end of the plunger is received within the barrel;

(iv) an annular second sealing wing encircling and radially projecting outward in a proximal direction from the exterior surface of the sidewall at an angle less than 90° relative to the longitudinal axis of the sealing cap, the second sealing wing being positioned proximal of the first sealing wing and contacting the interior surface of the barrel when the sealing cap attached to the head of the plunger is received within the barrel;

(v) an annular sealing ridge encircling and radially projecting out from the exterior surface of the sidewall between the fist sealing wing and the second sealing wing;

(vi) an interior surface defining a cavity within the sealing cap, the cavity being configured to complementary receive the head of the plunger, the cavity including an annular side groove configured to complementary receive the outer edge of the head of the plunger, the side groove being positioned relative to the annular sealing ridge so that the annular sealing ridge radially urges out to increasingly engage the interior surface of the barrel as the plunger is advanced within the barrel to increase the pressure within the barrel; and (vii) a annular end face positioned at the proximal end of the sealing cap and defining an opening to the cavity through which the head of the plunger is received within the cavity of the sealing cap.

49. A method for dispensing a fluid through a syringe, the method comprising the steps of:

(a) obtaining a syringe comprising:

(i) a barrel having an interior surface defining a lumen longitudinally extending between an access end and a discharge end;

(ii) an elongated plunger having a distal end slidably received within the access end of the barrel, the plunger further comprising a conical head positioned at the distal end of the plunger, the conical head radially sloping outward to an annular outer edge;

(iii) a flexible sealing cap mounted on the head of the plunger, the sealing cap comprising:

(A) an annular sidewall having an exterior surface extending between a proximal end and a distal end;

(B) a conical crown mounted on the annular sidewall so as to cover the distal end of the sealing cap;

(C) an annular first sealing wing encircling and radially projecting outward in a distal direction from the exterior surface of the sidewall at an angle less than 90° relative to the longitudinal axis of the sealing cap, the first sealing wing contacting the interior surface of the barrel when the distal end of the plunger is received within the barrel;

(D) an annular second sealing wing encircling and radially projecting outward in a proximal direction from the exterior surface of the sidewall at an angle less than 90° relative to the longitudinal axis of the sealing cap, the second sealing wing being positioned proximal of the first sealing wing and contacting the interior surface of the barrel when the sealing cap attached to the head of the plunger is received within the barrel;

(E) an annular sealing ridge encircling and radially projecting out from the exterior surface of the sidewall between the fist sealing wing and the second sealing wing;

(F) an interior surface defining a cavity within the sealing cap, the cavity being configured to complementary receive the head of the plunger, the cavity including an annular side groove configured to complementary receive the outer edge of the head of the plunger, the side groove being positioned relative to the annular sealing ridge so that the annular sealing ridge radially urges out to increasingly engage the interior surface of the barrel as the plunger is advanced within the barrel to increase the pressure within the barrel; and (G) an end face positioned at the proximal end of the sealing cap and defining an opening to the cavity through which the head of the plunger is received within the cavity of the sealing cap;

(b) attaching the discharge end of the barrel in fluid communication with to a fluid source;

(c) retracting the plunger from within the barrel so that the second sealing wing urges against the interior surface of the barrel so as to produce a seal that causes the fluid to flow into the barrel; and (d) advancing the plunger within the barrel so that the first sealing wing and the sealing ridge urge against the interior surface of the barrel to produce a seal that causes the fluid to discharge from the barrel though the discharge end.

* * * * *

UNITED STATES PATENT AND TRADEMARK OFFICE
CERTIFICATE OF CORRECTION

PATENT NO. : 5,735,825
DATED : Apr. 7, 1998
INVENTOR(S) : Brian W. Stevens; Darryl Kent Backman; Garlyn W. Hendry It is certified that error appears in the above-identified patent and that said Letters Patent is hereby corrected as shown below:

Col. 2, line 23, before "then" change "deliver" to --delivered--

Col. 2, line 34, after "typically" change "to do" to --do so--

Col. 6, line 59, after "against" change "conical face" to --conical inside surface--

Col. 7, line 8, after "not" delete --be--

Col. 7, line 53, after "In" change "ram" to --turn--

Col. 9, line 27, before "is" change "mm" to --turn--

Col. 10, line 31, after "sealing" insert --ridge-- and before "engage" insert --to--

Col. 10, line 49, before "112" change "edge" to --shoulder--

Col. 11, line 26, after "plunger" change "till" to --tip--

Col. 11, line 57, after "plunger" change "till" to --tip--

Col. 12, line 38, after "to" change "complementary" to --complementarily--

Col. 13, line 42, after "annular" delete the comma

Col. 15, line 48, after "to" change "complementary" to --complementarily--

Col. 15, line 55, after "(v)" change "a" to --an--

UNITED STATES PATENT AND TRADEMARK OFFICE
CERTIFICATE OF CORRECTION

PATENT NO. : 5,735,825

DATED : Apr. 7, 1998

INVENTOR(S) : Brian W. Stevens; Darryl Kent Backman; Garlyn W. Hendry

It is certified that error appears in the above-identified patent and that said Letters Patent is hereby corrected as shown below:

Col. 17, line 9, before "receive" change "complementary" to --complementarily--

Col. 17, line 16, after "(vii)" change "a" to --an--

Col. 18, line 19, after "to" change "complementary" to --complementarily--

Signed and Sealed this

Sixteenth Day of February, 1999

Attest:

Attesting Officer

*Acting Commissioner of Patents and Trademarks*